United States Patent [19]

Strom

[11] 4,438,284
[45] Mar. 20, 1984

[54] CATALYSTS FOR OXIDATIVE COUPLING OF PHENOLS

[75] Inventor: Robert M. Strom, Midland, Mich.

[73] Assignee: The Dow Chemical Company, Midland, Mich.

[21] Appl. No.: 378,674

[22] Filed: May 17, 1982

Related U.S. Application Data

[63] Continuation-in-part of Ser. No. 241,969, Mar. 9, 1981, abandoned.

[51] Int. Cl.$^3$ .............................................. C07C 39/14
[52] U.S. Cl. .................................... 568/730; 568/719
[58] Field of Search ............... 568/730, 723, 719, 726, 568/729; 260/396 N

[56] References Cited

U.S. PATENT DOCUMENTS

| | | | |
|---|---|---|---|
| 4,096,190 | 7/1978 | Rutledge | 568/730 |
| 4,098,830 | 7/1978 | Rutledge | 568/730 |
| 4,100,205 | 7/1978 | Rutledge | 568/730 |
| 4,101,561 | 7/1978 | Rutledge | 568/730 |
| 4,108,908 | 8/1978 | Rutledge | 568/730 |
| 4,132,722 | 2/1979 | Rutledge | 568/730 |
| 4,139,544 | 5/1979 | Earley | 568/730 |
| 4,195,189 | 3/1980 | Rutledge | 568/730 |
| 4,354,047 | 10/1982 | Strom | 568/730 |
| 4,354,084 | 10/1982 | Strom | 568/730 |
| 4,361,708 | 11/1982 | Strom | 568/730 |

FOREIGN PATENT DOCUMENTS 536277  10/1931  Fed. Rep. of Germany ...... 568/730

OTHER PUBLICATIONS

Hudec, "Journal of Catalysis", vol. 53, pp. 228–231 (1978).
"The Encyclopedia of Chemistry", 3rd ed. Reinhold (1973), N.Y., pp. 209–213.
Plummer "Bertchte", vol. 59, pp. 2159–2175 (1926).
Clemo et al., "J. Chem. Soc." (1931), pp. 1265–1273.
Taylor et al., "Oxidative Coupling of Phenols" Marcel Inc. N.Y., pp. 1–51, 80–95 (1967).
Cook et al., "J. Org. Chem.", vol. 23, p. 755 (1958).
Matthews et al., "J. Org. Chem.", vol. 25, p. 264 (1960).

*Primary Examiner*—Werren B. Lone
*Attorney, Agent, or Firm*—Douglas N. Deline

[57] ABSTRACT

Self-condensation products are obtained by the oxidative coupling of substituted phenols in the presence of a heterogeneous cobalt-containing catalyst.

14 Claims, No Drawings

CATALYSTS FOR OXIDATIVE COUPLING OF PHENOLS

CROSS-REFERENCE TO RELATED APPLICATION

This is a continuation-in-part of copending application Ser. No. 241,969, filed Mar. 9, 1981, now abandoned.

BACKGROUND OF THE INVENTION

The invention relates to an improved method of producing binary self condensation products of phenols. It is well-known in the art that substituted phenols can be oxidized to yield self-condensation products, especially diphenoquinones, biphenols and polyphenylene oxides. The diphenoquinones are useful antioxidants. Biphenols are useful antioxidants, stabilizers and intermediates for the synthesis of various polymers, especially polyesters. Polyphenylene oxides comprise a useful class of polymeric materials having utility as molding resins, extrusion resins, etc.

In U.S Pat. No. 4,195,189, a one-step process for the oxidative coupling of phenols is described wherein molten phenols are combined with an oxidizing agent which is activated copper oxide. The copper oxide was employed in about equal or greater molar ratio with the phenolic compound. In this process the copper oxide is employed not as a catalyst but as a source of oxygen as no oxygen or oxygen-containing gas is otherwise present during the reaction.

In German Pat. No. 536,277, the oxides of copper, manganese and lead were employed in the oxidative reaction of phenol. The reaction product was most probably a polymeric material, however was not identified. The product was a light grey amorphous precipitate without a sharp melting point which sintered to a brown mass at 120° C. to 130° C. Diphenoquinone is a highly colored crystalline material which decomposes at about 165° C. Polyphenylene oxide in its higher molecular weights is a tough white solid that has glass transition temperatures in excess of 200° C.

SUMMARY OF THE INVENTION

The present invention comprises an improved process for the oxidative coupling of phenols to prepare diphenoquinones, biphenols and polyphenylene oxides. Accordingly, diphenoquinones, biphenols and polyphenylene oxides are prepared by carbon-carbon or carbon-oxygen coupling in accordance with the following general reactions depending on the reactive sites available in the phenol employed.

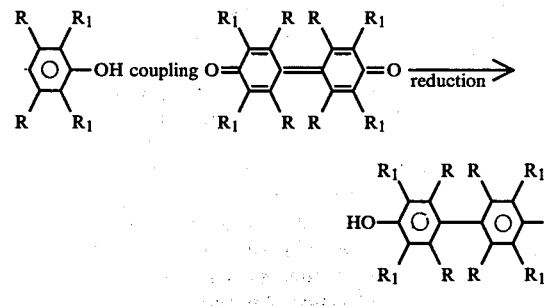

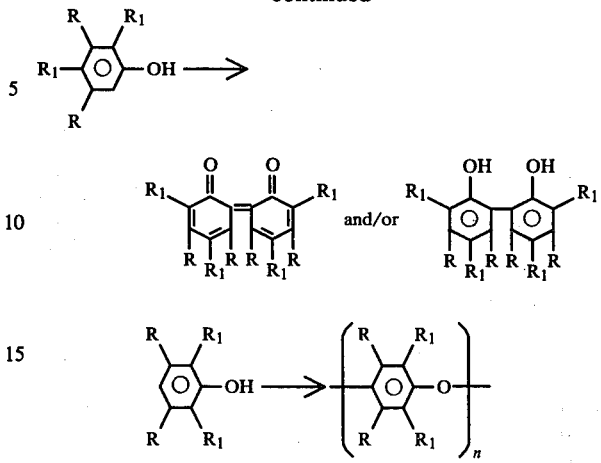

Each R is either hydrogen, halogen or $R_1$, and each $R_1$ is a substituent having up to 10 carbons selected from hydrocarbon, halohydrocarbon or hydrocarbonoxy. Preferred phenol reactants are 2,6-disubstituted phenols which couple to form 3,3',5,5'-tetrasubstituted-p,p'-diphenoquinones. Most preferred are 2,6-dialkyl-substituted phenols. The phenol reactants are contacted in the presence of oxygen or an oxygen-containing gas with a heterogeneous catalyst comprising cobalt. The reaction is preferably conducted at elevated temperatures and pressures.

The diphenoquinone reaction products, where produced, may be reduced by contact with a heterogeneous hydrogenation catalyst to produce the corresponding biphenol, if desired. Also, if desired, where R is hydrogen and each $R_1$ is an alkyl group that is easily removable, the substituted biphenol may be dealkylated according to the invention to produce an unsubstituted biphenol. Suitable easily removable alkyl groups include tertiary butyl or tertiary amyl.

Where polyphenylene oxides are prepared, they too may be dealkylated if desired, but are generally employed as prepared.

DETAILED DESCRIPTION OF THE INVENTION

The substituted phenol reactants here used are those well-known in the art as forming oxidative carbon-to-carbon coupling products. Examples are 2,6-dimethyl phenol, 2,6-diethyl phenol, 2,6-ditertiary butyl phenol, 2,6-diisobutyl phenol, 2-octyl-6-methyl phenol, 2,6-ditertiary-hexyl phenol, 2-ethyl-6-methyl phenol, 2-methyl-6-tertiary butyl phenol, 2-cyclohexyl-6-methyl phenol, 2,6-dimethoxy phenol, 2,6-dibutoxy phenol, 2-methoxy-3-ethoxy-6-methyl phenol, 2,4-dimethyl phenol, 2,4-ditertiary butyl phenol, 2-methyl-4-amyl phenol, 2-methyl-4-ethoxy phenol, 2-ethoxy-3,4-dimethyl phenol, 2,4-dimethyl-3,5-dichlorophenol, etc. Because of steric hinderance, when the 2,4-substituted phenolic compounds are coupled in the ortho position, the substituent on the 3-position is preferably hydrogen, halogen or a short-chain alkyl group. Generally like phenol compounds are coupled to reduce the variety of reaction products formed, unless of course a mixture of products is acceptable. The preferred phenolic reactant, in order to prepare carbon-carbon coupled reaction products, is 2,6-ditertiary butyl phenol. Where polyphenylene ethers are desired, a phenolic compound having less sterically hindered substituents is generally employed. Preferred is 2,6-dimethylphenol.

The oxygen used is either oxygen itself or an oxygen-containing gas such as air. While any suitable pressure from atmospheric to elevated pressures may be employed, it is preferred for carbon-carbon coupling, in order to produce improved reaction rates and yields, to employ elevated pressures. The reaction is normally conducted in a pressurized system with the oxygen-containing gas supplying the pressurizing means. Elevated pressures of up to about 500 psig may be employed depending on the amount of oxygen present in the gas mixture and the pressure vessel design limits. Utilizing air as the oxidizing medium pressures of about 100–450 psig are suitable. When it is desired to prepare polyphenylene ethers, lower pressures are employed. Suitable pressures are from atmospheric to about 100 psig. Often in the preparation of polyphenylene ethers, small amounts of carbon-carbon coupled reaction products are also formed.

The reaction is conducted at elevated temperatures of from about 30° C. to about 200° C., preferably from about 50° C. to about 150° C. and most preferably from about 60° C. to about 100° C. for the time necessary to form substantial amounts of the desired tetra-substituted coupled reaction product.

The process may be operated without a solvent, interchangeably referred to herein as a liquid reaction medium, in which case the substituted phenol itself acts as a solvent. However, preferably a liquid reaction medium is employed in order to aid in transport of reactants and in recovery of the products. Any liquid under the reaction conditions that is relatively unreactive is acceptable. The reactants and products need not be highly soluble therein and indeed may be insoluble. Examples include such organic liquids as lower carboxylic acids, alcohols, and aromatic compounds. Preferred solvents may differ depending on the nature of the phenol reactant, the catalyst and the reaction conditions employed. Particularly, preferred liquids are polar compounds, particularly lower alcohols which are not themselves easily oxidizable. An example is methanol. These polar liquids tend to stabilize the cobalt oxide catalysts. In the preparation of polyphenylene ethers, it is preferred to employ aromatic solvents such as toluene or chlorinated benzenes such as ortho-dichlorobenzene. In such solvents the polyphenylene ether is soluble and may be easily separated from the catalyst and from diphenoquinone by-products that may also be produced by the process.

The catalysts employed are heterogeneous catalysts comprising cobalt. The cobalt is present in active form in an oxidation state suitable to catalyze the desired oxidative coupling reaction. In its active catalytic state the cobalt is active as a dehydrogenation catalyst and is preferably present as the oxide. A particularly preferred catalyst comprises a mixture of the oxides of cobalt and copper. The catalytic effectiveness of this catalyst has been found to be improved over either cobalt oxide or copper oxide alone thereby providing a synergistic effect.

In the particularly preferred catalyst, the proportions of cobalt oxide and copper oxide may vary over a wide range. Molar ratios of cobalt to copper from 1:9 to 9:1 are suitable, with about a 1:1 molar ratio being particularly suitable. The catalysts may be prepared merely by precipitating the corresponding metal hydroxides from aqueous solution of the soluble salts followed by heating to produce the corresponding oxides. An inert substrate such as carbon, silica, alumina, diatomaceous earth, clays, etc., may also be employed to provide increased surface area for the catalyst. The substrate may be added to the aqueous solution prior to precipitation of the catalyst therefrom thereby producing a surface coating onto the substrate of the desired catalyst or alternatively the aqueous mixture may be evaporated to dryness leaving the substrate coated with the desired metal compound. Heating to elevated temperature readily produces the desired supported metal oxide catalyst.

In the operation of the invention, the heterogeneous cobalt-containing catalyst is placed into a suitably designed reactor vessel fitted with a reactant inlet and product outlet along with heating means as well as an entrance and exit means for the oxygen-containing gas. The reactor vessel is charged with a solution of a substituted phenol in the previously described liquid reaction medium. In a batch operation, the reactor is then sealed and heated to the desired reaction temperatures accompanied by oxygen addition. Agitation, as for example by stirring, may also be employed. In a continuous operation, the reactant charge is supplied to a reactor containing the catalyst that is maintained at the desired temperature. A stream of oxygen-containing gas is also supplied to the reactor either concurrently or countercurrently and the product mixture is continuously removed.

The coupled phenol in the product mixture is separated from unreacted substituted phenol if necessary and may even be separated from the liquid reaction medium as by distillation or precipitation. Where carbon-carbon coupled reaction products are prepared, e.g., substituted diphenoquinones, preferably the crude mixture containing substituted diphenoquinone is further charged to a second reactor containing a heterogeneous hydrogenation catalyst maintained under reducing conditions. Suitable hydrogenation catalysts are those heterogeneous hydrogenation catalysts previously known in the art, such as the noble metals, nickel, etc. The reaction conditions employed are substantially modified from the oxidative coupling conditions initially employed in order to effect the desired hydrogenation. Generally, the hydrogenation is conducted at temperatures from about 25° C. to about 150° C. and pressures from about atmospheric to about 100 psig in the presence of a hydrogen-containing gas.

Alternatively, the reduction may be accomplished by reacting the diphenoquinone with additional phenol, or unreacted phenol from the oxidative coupling reaction in the presence of base at an elevated temperature as is previously known in the art and taught, for example, in U.S. Pat. No. 3,562,338 which teaching is incorporated herein by reference.

The hydrogenation product is the corresponding substituted biphenol which may be recovered from the reaction mixture. As previously mentioned, for the preparation of carbon-carbon coupled reaction products, each $R_1$ is an alkyl group which may be removed by a suitable dealkylation process. Removal of such alkyl groups from the biphenol product, if desired, is accomplished according to well-known techniques. One suitable method is to heat the substituted biphenol at an elevated temperature below the decomposition temperature of the biphenol. This process is described and taught in U.S. Pat. No. 4,205,187 which teaching is incorporated herein by reference. Another process particularly effective when the alkyl groups are tertiary butyl or tertiary amyl, is to heat the alkylated biphenol in the presence of a catalytic amount of a strong acid such as p-toluene sulfonic acid. The alkyl group is effectively removed to yield the respective alkene, e.g., isobutene in the case of tertiary butyl groups, pentenes when tertiary amyl groups are employed, and the desired dealkylated biphenol product.

The isobutene or similar alkene so obtained may be recycled if desired to alkylate phenol itself resulting in production of the substituted phenols originally employed in the instant oxidative coupling step. The alkylation of phenols in this manner is well-known technology. Suitably, the phenol may be readily selectively alkylated by forming first the aluminum phenoxide which is then reacted by contacting with isobutene at elevated pressure and temperature. This process is well-known having been previously described in U.S. Pat. No. 2,831,898 which teaching is herein incorporated by reference.

The instant process allows for a large degree of flexibility in operation, particularly for the preparation of carbon-carbon coupled products. The catalyst may be packed into a fixed bed inside a pressure reactor. It is further possible in a continuous process to employ several reactors, one for the oxidative coupling step and the other for the hydrogenation. The substituted phenol is reacted in the presence of oxygen to form diphenoquinone in the first reactor and subsequently the reaction mixture is charged to the second reactor where it is reduced preferably by the action of hydrogen.

SPECIFIC EMBODIMENTS

Having described my invention, the following examples are provided as illustrative of the invention and are not to be construed as limiting.

Example 1—Catalyst Preparation

An aqueous solution containing equal molar amounts of copper and cobalt ions was prepared. Accordingly, $Co(NO_3)_2 6H_2O$ (238 g, 0.818 mole) was combined with $Cu(NO_3)_2 2.5H_2O$ (190.3 g, 0.818 mole) in 3.5 liters of water. The solution was slowly added to a concentrated solution of $NH_4CO_3$ (3 liters) while maintaining the solution at a pH of from about 6.5 to about 7.0. A precipitate formed which was washed with water and heated to 300° C. for 1.5 hours. The mixture of cobalt oxides and copper oxides was then compacted by pelletizing and the pellets subsequently crushed to a powder.

Example 2—Catalyst Preparation

A cobalt oxide catalyst was prepared by substantially the same process as was employed in Example 1. Accordingly, $Co(NO_3)_2 6H_2O$ was dissolved in water and the corresponding hydroxide precipitated by addition to a $NH_4CO_3$ solution maintained at pH 6.5. The resulting precipitate was filtered, dried and calcined as previously explained in Example 1.

Example 3

In a 300-ml nickel parr reactor, 2,6-ditertiary butyl phenol (25 g) was combined with 1.25 g of the cobalt oxide catalyst prepared in Example 2 in 50 ml of methanol and a small amount of $Na_2CO_3$ (approx. 0.1 g). The reactor was sealed and pressurized to 250 psig with oxygen. The reactor was then heated to about 75° C.-80° C. for one hour while being stirred. After cooling to room temperature, the product mixture was analyzed by gas-liquid chromatography and found to contain 84.2 percent of 3,3', 5,5'-tetratertiary butyl diphenoquinone. About 11.6 percent of initial reactant remained. By-products comprised principally 2,6-ditertiary butyl-1,4-benzoquinone, 2.8 percent, and 1.4 percent of 2,4-ditertiary butyl phenol, an isomer of the initial reactant.

Example 4

The reaction conditions of Example 3 were substantially repeated employing 1.25 g of the cobalt oxide-copper oxide catalyst of Example 1. After reaction for about 1 hour at a temperature of about 75° C.-80° C., the reaction mixture was again analyzed by gas-liquid chromatography and found to contain about 98.1 percent of 3,3', 5,5'-tetratertiary butyl diphenoquinone. Only 0.5 percent unreacted 2,6-ditertiary butyl phenol remained and by-products consisted of 0.6 percent 2,6-ditertiary butyl-1,4-benzoquinone and 0.8 percent of 2,4-ditertiary butyl phenol.

Example 5

By comparison, the reaction conditions of Example 4 were substantially repeated employing a prior art precipitated copper oxide catalyst made according to the procedure of Example 2. After reaction for 1 hour, according to the procedures of Example 3 or 4, the reaction mixture consisted of only 29.2 percent 3,3', 5,5'-tetratertiary butyl diphenoquinone. The remainder comprised 68.7 percent of unreacted 2,6-ditertiary butyl phenol, 0.7 percent 2,6-ditertiary butyl-1,4-benzoquinone and 1.4 percent 2,4-ditertiary butyl phenol.

Example 6—Polyphenylene Ether 2,6-Dimethylphenol (20 g), toluene (100 ml) and the cobalt-copper catalyst of Example 1 (1.25 g) were charged to a 300-ml parr reactor. The reactor was sealed and pressurized with oxygen to 50 psig. The reactor was then heated to 100° C. for about 9 hours.

After heating for the indicated time period, the pressure was released and the reactor contents removed. Solids including 3,3', 5,5'-tetramethyldiphenoquinone and catalyst were removed by filtration. The toluene was removed by evaporation to leave 15.3 g of a coherent solid polyphenylene ether polymer having average molecular weight of about 1,000 as determined by gel permeation chromatography.

What is claimed is:

1. A process for preparing by an oxidation coupling reaction a carbon-carbon coupled or carbon-oxygen coupled condensation product of a substituted phenol of the formula

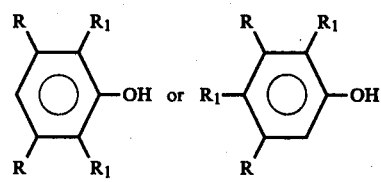

wherein each R is hydrogen, halogen or $R_1$, and each $R_1$ is a substituent having up to 10 carbons selected from the group consisting of hydrocarbon, halohydrocarbon and hydrocarbonoxy comprising contacting the substituted phenol with an oxygen-containing gas under oxidative coupling conditions in the presence of a heterogeneous catalyst comprising cobalt present in an oxidation state suitable for forming oxidatively coupled reaction products.

2. A process according to claim 1 wherein the substituted phenol is a 2,6-dialkyl phenol.

3. A process according to claim 1 wherein the catalyst comprises an oxide of cobalt.

4. A process according to claim 1 wherein the catalyst additionally comprises an oxide of copper.

5. A process according to claim 3 wherein the catalyst is supported by an inert supportive means.

6. A process according to claim 5 wherein the inert supportive means is alumina, carbon, silica, diatomaceous earth or clay.

7. A process according to claim 3 wherein the catalyst consists essentially of a mixture of the oxides of cobalt and copper.

8. A process according to claim 1 or 7 wherein an inert liquid reaction medium is also present.

9. A process according to claim 8 wherein the inert liquid reaction medium is a polar compound.

10. A process according to claim 9 wherein the inert liquid reaction medium is methanol.

11. A process according to claim 1 which is conducted at a temperature from about 30° C. to about 200° C. and at an elevated pressure of up to about 500 psig.

12. A process according to claim 2 wherein the substituted phenol is 2,6-ditertiary butyl phenol and the condensation product is 3,3', 5,5'-tetratertiarybutyl diphenoquinone.

13. The process according to claim 12 wherein the 3,3', 5,5'-tetratertiarybutyl diphenoquinone is thereafter reduced.

14. The process according to claim 13 wherein the reduction is accomplished by contacting the 3,3', 5,5'-tetratertiarybutyl diphenoquinone with hydrogen-containing gas in the presence of a heterogeneous hydrogenation catalyst at a temperature from about 25° C. to about 150° C. and pressures from about atmospheric to about 100 psig.

* * * * *